(12) United States Patent
Trotti, III

(10) Patent No.: US 8,275,552 B1
(45) Date of Patent: Sep. 25, 2012

(54) TOXICITY REPORTING SYSTEM

(75) Inventor: Andrea Trotti, III, Tampa, FL (US)

(73) Assignee: University of South Florida, Tampa, FL (US)

( * ) Notice: Subject to any disclaimer, the term of this patent is extended or adjusted under 35 U.S.C. 154(b) by 1667 days.

(21) Appl. No.: 10/711,806

(22) Filed: Oct. 6, 2004

Related U.S. Application Data

(60) Provisional application No. 60/481,472, filed on Oct. 6, 2003.

(51) Int. Cl.
*G06F 7/00* (2006.01)
(52) U.S. Cl. .............. 702/19; 702/20; 703/11; 707/700; 435/6.1
(58) Field of Classification Search .................. None
See application file for complete search history.

(56) References Cited

U.S. PATENT DOCUMENTS 6,177,940 B1 * 1/2001 Bond et al. .................... 434/262
6,270,456 B1   8/2001 Iliff

OTHER PUBLICATIONS

Trotti (Int J Radiation Oncology Phys vol. 47, No. 1 pp. 1-12, 2000).*
Trotti, A.; Pajak, T. F.; Gwede, C. K.; Paulus, R.; Cooper, J.; Forastiere, A.; Ridge, J. A.; Watkins-Bruner, D.; Garden, A. S.; and, K. K.; Curran, W. TAME: development of a new method for summarising adverse events of cancer treatment by the Radiation Therapy Oncology Group. The Lancet Oncology. 2007. vol. 8: pp. 613-624.
National Cancer Institute Fact Sheet. Staging: Questions and Answers. National Cancer Institute. Jan. 6, 2004. pp. 1-5.

* cited by examiner

*Primary Examiner* — Mary Zeman
(74) *Attorney, Agent, or Firm* — Molly L. Sauter; Smith & Hopen, P.A.

(57) ABSTRACT

The present invention is a method for communicating and forecasting the extent of toxicity of a given treatment program by deploying a uniform multi-modality grading system, and capturing significant high-grade events within defined risk periods to create a treatment-specific summary rating or classification of the toxicity experience.

10 Claims, 3 Drawing Sheets

Fig. 2

| TAME scores | Outcome endpoints |
|---|---|
| Generated from individual patient data on each grade 3-4 event experienced during treatment and follow-up | Completion of treatment<br>QOL<br>Performance status<br>Physician perception<br>Patient perception<br>Key symptoms index |

TOXICITY REPORTING SYSTEM

CROSS REFERENCE TO RELATED APPLICATIONS

This application claims priority to U.S. Provisional Patent Application No. 60/481,472, "Toxicity Reporting System", filed Oct. 6, 2003.

BACKGROUND OF INVENTION

The patient with cancer faces two threats: the cancer itself and the cancer treatment. An unwelcome organism has arisen from within and it needs to be removed or dissolved. One of the personal costs of cancer treatment is the adverse effect of treatment, and it is among the highest price tags in all of medicine. The patient wants to know, "what will the cancer do to me if it is not treated" and "what will the treatment do to me?" The physician uses different terms to ask the same questions: what are the odds of survival and toxicity with each treatment option. In clinical terms, both parties want to know the impact of cancer and its treatment on the "host". Both threats can result in illness or death.

The management of cancer often involves making choices among various treatment options, some of which are more toxic than others. The degree of "aggressiveness" of a treatment program is currently ill defined, but is generally proportional to the amount of toxicity. The "tolerance" of a regimen is a general perception by the clinician relative to other treatments for the same category of patients, and may focus on a single treatment-limiting organ, e.g., bone marrow. In general, the greater the threat of the disease to life, organ function or severity of discomfort from the disease, the more risk or ill effects one is willing to consider in order to counter the disease. An attempt is made to match treatment intensity to the severity of disease, but there are no suitable metrics to guide that decision-making. Currently, in the art there does not exist a method to ascertain if the toxicity of a given treatment is "acceptable" or not. Accordingly, no formal numbers can be applied to calculate a so-called "therapeutic ratio" relating the treatment effectiveness to the treatment toxicity.

Oncology is a unique and suitable model for development of better adverse effects reporting methods as well as a classification system for toxicity. It is one of the only fields of medicine where not only are many of the agents highly toxic, but they are used in combination, at times with radiation and surgery, generating multiple significant toxicities in the same patient. For non-oncology drugs, a given patient may experience 1 or 2 side effects at most, and these are usually mild in nature. Drug warning labels generally contain a list of possible adverse effects, with frequencies rarely over 10-20%. Severe side effects are usually rare, and life-threatening ones are extremely rare. In oncology, it is not uncommon to see rates of grade 3-4 effects in the 50-60% range with a conclusion that the regimen was "well tolerated". Death rates of 1-3% are routinely accepted in aggressive regimens, and mortality has approached 30% in some bone marrow transplant studies.

Modern cancer therapy employs multiple aggressive treatment modalities associated with significant short and long-term morbidity. Balancing the cancer itself and the cancer treatment for a net therapeutic benefit is a judgment that requires reliable and readily interpretable information regarding both survival and toxicity. Interpreting toxicity information in oncology is a difficult task, for both the patient and the physician. For even a single trial, there is a large amount of toxicity information to digest, and no associated method of summarizing this data into a readily interpretable and useful statement. This is aggravated by gaps and inconsistencies in current reporting methods that make it nearly impossible to compare adverse outcomes between studies or among treatment options. This is in sharp contract to the ability to describe prognosis, which includes multiple well-defined endpoints and sophisticated analytical tools. Scientists have developed a common language to characterize and communicate the wonders of the human genome, but we cannot effectively communicate to our patients the full scope of risk from cancer treatment. As such, the adverse effects reporting process is comparatively under-developed, and there has been no organized effort to advance it. At a practical level, only half of the therapeutic ratio is defined, thereby limiting the ability to make informed judgments about risks and benefits of treatment protocols.

Quantifying the negative impact of cancer treatment on health has been difficult. One major factor is the myriad expressions of ill effects. As currently codified in the National Cancer Institute-Common Terminology Criteria (NCI-CTC v 3.0), there are more than 500 distinctly recognizable types of injury or symptoms, each with 4 grades of severity, resulting in more than 2000 definable ill effects. The duration and number of episodes of each event adds to the perception of toxicity burden. Some ill effects occur in a repetitive fashion with each cycle of treatment and others can cause permanent changes, which may last a lifetime.

The TNM (Tumor, Nodes, Metastases) tumor staging system was developed more than 40 years ago. The TNM system gauges the severity of cancer on an escalating scale. It has been widely adopted and used to stage more than 30 million cancer patients in the U.S. since its inception. It is routinely applied to the majority of solid tumors and more than 70% of all cancers. More than 500,000 patients in the U.S. are staged annually. In 1990 it was harmonized with the international staging system (IUCC) to represent one of the most valuable tools in cancer epidemiology and treatment-related decision-making worldwide. It has undergone periodic revisions as new technologies or interventions have altered outcomes.

The TNM system has three components or domains. T (tumor) represents the local extent and invasiveness of the primary cancer. N (node) represents the extent of nodal spread, and M (metastasis) represents the presence or absence of metastatic disease. Limiting it to three simple factors is in large part why the TNM system has been so well adopted and enduring. However, each tumor site uses different T and N criteria, based on their own unique behavior. Indeed, the specific rules and terms for staging each site are quite distinct and elaborate, requiring a large staging manual and special training. Cancers may be staged clinically or surgically (pathologically) or a mixture of the two.

The TNM system also has limitations, which have been recognized. This system reflects only the anatomic extent of disease and does not include other known prognostic factors such as histological type, grade, age, sex, co-morbid illness or duration of symptoms. It does not include biologic factors, which may also be prognostic. Each T, N, and M domain reflects a conceptual progression of cancer by estimating its true anatomic extent. It does not include direct measures of the number of cancer cells or any direct measures of the impact of the cancer on the host (symptoms or other effects). Although it is generally prognostic for survival and tumor control, it is actually only a rough estimate of the extent of cancer. Additionally, the TNM system does not communicate and forecast the extent of toxicity of a given treatment program.

Accordingly, what is needed in the art is a method for summarizing the complexities of the toxicity experience associated with a variety of disease conditions, including cancer. Such a method would provide for the reduction of a large quantity of toxicity data from a given treatment program into a summary statement which captures the important features of global or aggregate toxicity burden. Such a method should have wide applications to many facets of oncology and other fields of medicine.

However, in view of the prior art considered as a whole at the time the present invention was made, it was not obvious to those of ordinary skill in the pertinent art how the identified need could be fulfilled.

SUMMARY OF INVENTION

The longstanding but heretofore unfulfilled need for a system and method designed to summarizes the complexities of the toxicity experience associated with cancer is now met by a new, useful, and nonobvious invention.

In accordance with the present invention is provided a system and method for communicating and forecasting the extent of toxicity of a given treatment program. Beginning with the use of a uniform multi-modality grading system, and capturing significant high-grade events within defined risk periods, one can create a treatment-specific summary rating, or classification, of the toxicity experience referred to as the TAME score.

In a particular embodiment, the method in accordance with the present invention for determining a toxicity rating of a treatment program includes, identifying a uniform multi-modality grading system, capturing significant events occurring within predetermined periods based on the uniform multi-modality grading system, determining the toxicity rating of the treatment program from an aggregation of the captured significant events. The uniform multi-modality grading system used in accordance with the present invention may be the National Cancer Institute Cancer Toxicity Criteria system, or other toxicity grading system known in the art.

In a particular embodiment of the invention, an acute toxicity domain of the treatment program, an adverse late effects domain of the treatment program and a risk of treatment related mortality domain of the treatment program are determined and the acute toxicity domain, the adverse late effects domain and the risk of treatment related mortality domain are aggregated resulting in a toxicity rating of the treatment program.

The toxicity rating may be employed in the field of oncology or other medical fields exhibiting toxicity related events.

The acute toxicity domain of the treatment program is the acute toxicity experienced by a patient surrounding the course of the treatment program and may be further defined as a median number of significant acute effects in a patient group during the treatment program for a predetermined risk period. The predetermined risk period may be determined on a case-by-case basis. In a specific embodiment, the predetermined risk period is from day one of the treatment program through three months in duration of the treatment program.

The adverse late effects domain of the treatment program is the late toxicity experienced by a patient after the treatment program and may be further defined as a median number of adverse late effects in a patient group during the treatment for a predetermined risk period. The predetermined risk period may be determined on a case-by-case basis. In a specific embodiment, the predetermined risk period is greater than three months of duration of the treatment program.

The risk of treatment related mortality domain is further defined as the risk of mortality from the treatment program.

In an additional embodiment, a mathematical weight may be assigned to the acute toxicity domain, the adverse late effect domain and the risk of treatment related mortality as deemed necessary.

In yet another embodiment, a therapeutic ratio for the treatment program may be determined. The therapeutic ratio being equal to the survival rate associated with the treatment program divided by the determined toxicity rating.

The toxicity rating in accordance with the present invention is referred to by the acronym "TAME". The TAME system is a method of aggregating toxicity data collected in clinical trials. Immediate validation of the TAME system can be performed, retrospectively, on existing data sets, via outcome analysis. Full implementation will not require addition of new tools or instruments to the current reporting process, but interim validation would be facilitated by surveys of patient and physician perceptions of toxicity profiles and QOL data. In addition, improvements in the data collection process are suggested to facilitate uniformity in data collection methods and to ensure capture of clinically important endpoints by all investigators. The TAME system should also eventually facilitate the establishment of adverse effects reporting standards and publishing guidelines.

The benefits of a toxicity staging system are numerous and include: improved patient counseling and decision making in cancer treatment selection; calculation of truly quantitative therapeutic ratios and other new metrics; evaluation of palliative treatment options; individual monitoring of toxicity during treatment; a new safety reporting metric for sponsors, data monitoring committees, and Institutional Review Boards; pooling of toxicity data across multiple studies to improve the precision of risk estimates; facilitating the development and selection of toxicity interventions; and providing an important new quality assurance metric.

Improving toxicity reporting will require the coordinated planning and collaboration of multiple organizations, regulatory agencies, and cooperative groups. It will require some increased attention to toxicity data collection in the clinic. However, the payoff for this investment could have a substantial and wide ranging impact on cancer research and cancer care.

BRIEF DESCRIPTION OF DRAWINGS

FIG. 2 is a table illustrating a number of clinical outcomes correlated the system in accordance with the present invention.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Figure 1:
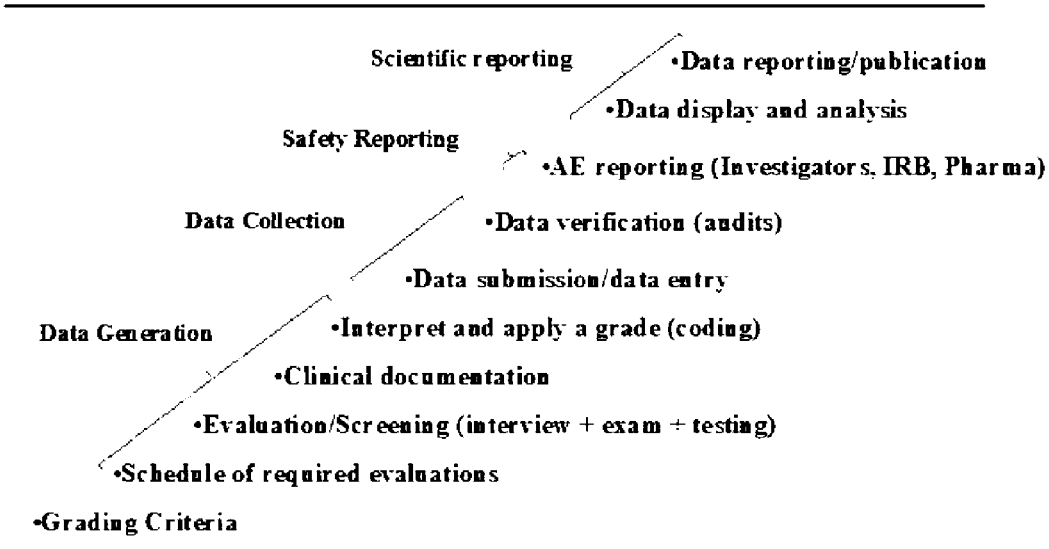
FIG. 1 illustrates the toxicity reporting process for generating and communicating adverse effects information, including text steps and four phases.
Figure 3:
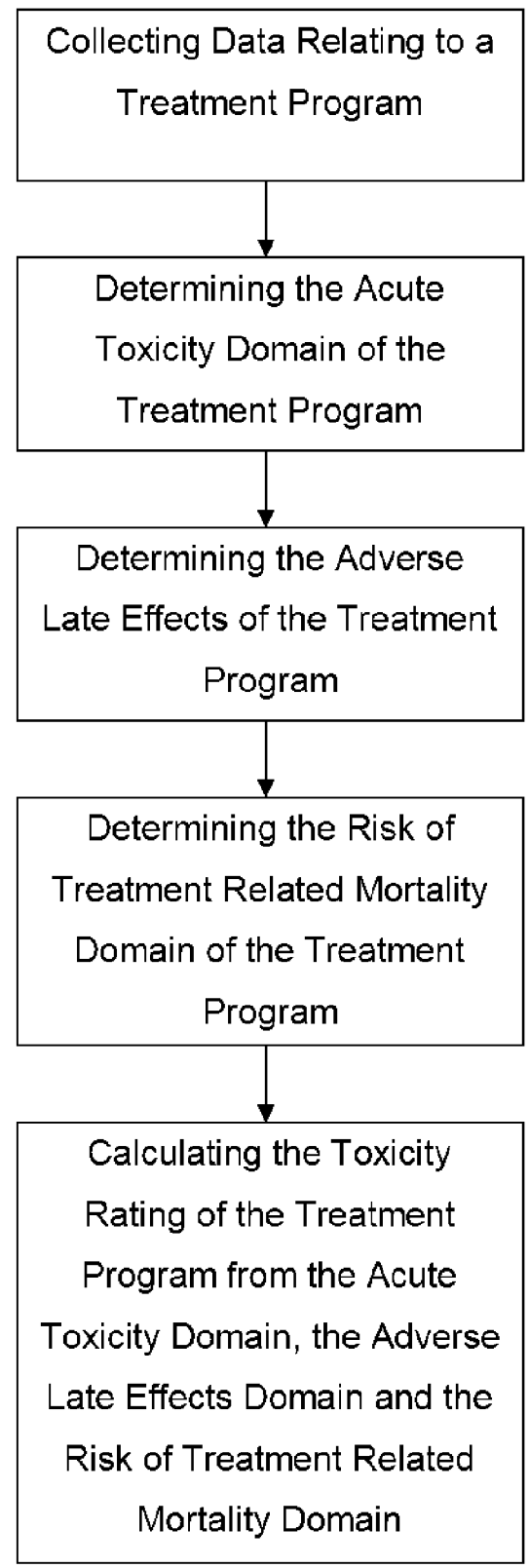
FIG. 3 is a flow diagram illustrating the method in accordance with the present invention.

With reference to FIG. 1, the toxicity reporting process for generating and communicating adverse effects information is illustrated and described as including ten steps and four phases.

After more than 30 years of multiple iterations and evolution, the National Cancer Institute (NCI) recently developed a single comprehensive grading dictionary that may be used by all modalities for capturing the adverse acute and late effects of cancer treatment, National Cancer Institute Cancer Therapy Evaluation Program, CTCAE v 3.0 (CTEP website). The CTCAE system consists of more than 500 distinctly recognizable signs and symptoms, each graded on a 4-point scale.

In accordance with a particular embodiment, using the TNM tumor staging system analogy, the "extent" or "global impact" of toxicity is to be considered as a combination of 3 clinically relevant domains: acute toxicity (T), adverse late effects (A), and the risk of treatment related mortality (M). Each domain reflects an important dimension of the toxicity experience, or the risk thereof. Just as each tumor site requires a different tumor staging system and end results, the toxicity of each treatment program needs to be considered within the context of a given site and stage of disease. The toxicity generated by a given treatment for advanced stage head and neck cancer should not be compared to that for a prostate cancer treatment program. However, the toxicity of a given treatment program for advanced head and neck cancer can be compared to the toxicity of other head and neck treatment options for the same or similar stage.

The system and method in accordance with the present invention is a new method of aggregating and analyzing data routinely collected in clinical trials. As such, future implementation of the system and method will not require the introduction of new tools or instruments for use in gathering data and all effects will be coded and graded for severity using the NCI-CTC grading system.

In an exemplary embodiment of the invention, the components of the system in accordance with the present invention are defined as:

T=the median number of grade 3-4 acute effects in a patient group during a given treatment program for risk period 1: day 1 thru ~3 months (exact time frames to be defined by site), "T" will therefore represent the acute toxicity experienced by a "typical" patient surrounding the course of treatment. Rules for counting prolonged or ongoing effects will be developed. In general, most severe events of long duration e.g., mucositis, would only be counted once during this period. However, each recurring grade 4 (e.g., life-threatening neutropenia) effect would be counted.

A=the median number of grades 3-4 late effects in a patient group after a given treatment program for risk period 2: beyond 3 months. "A" will therefore represent the late toxicity experienced by a "typical" patient after treatment. Again, exact time frames for each risk period will be determined per disease site, analogous to the development of cancer staging rules. It may be useful to define several late risk periods depending on the disease and normal tissue effects trajectory, especially for certain populations such as pediatrics. For example, A=less than 3 years; A'=3 or more years after treatment years.

M=the risk of mortality (in %) from cancer treatment at anytime during or after treatment for an unlimited time period.

In accordance with the present invention, the sum of the values for the 3 basic domains outlined above, T, M and A, will be considered a combined "End-results" summary score (TAME). As such the TAME score in accordance with the present invention will be represented by:

$$TAME(composite\ score) = T + A + M$$

It is recognized that this formula mixes numbers of different dimensions (median # of events and incidence). For now, this will be accepted for the sake of simplicity. The weighting of these components and other potential mathematical manipulations will also be explored through data analytic methods, but at this time a simple summation is proposed. It may be useful to combine only acute and late toxicity with this system and report mortality separately. Assumptions will need to be made regarding the inclusion and/or weighting of mortality.

In addition to the median number of events experienced by a group of patients, knowing the range of and number of events and outliers may be of clinical value. This would be provided separately from the composite TAME score.

In accordance with an additional embodiment, rules are used developed to combine the toxicity of "salvage treatment" to that of the initial treatment, so that the entire burden of toxicity associated with organ preservation approach can be reported. This will use a method similar to that described for multi-cycle chemotherapy extending beyond 3 months as described above.

As such, the TAME classification system in accordance with the present invention is a method of collecting the "significant" adverse effects into a composite score which reflects the global or aggregate toxicity associated with a given treatment program. It does not include all toxicity events, which can be readily represented by in other ways such as incidence tables. As such, TAME scores are to be used in addition to traditional reporting methods such as incidence rates. However, since patients who experience high-grade effects also experience some low-grade effects, TAME scores will be proportional to the true aggregate toxicity burden.

By focusing on grade 3-4 effects, the present invention is designed to function within the context of treatment programs of moderate to high toxicity. However, depending on the disease site and aggressiveness of treatment programs, one could define "significant" to include middle and/or lower grade effects to reflect the key features of toxicity experiences of various intensities.

By providing the number of significant events a patient is likely to experience in each time frame, in addition to information on the types and incidence of each potential toxicity, one should be able to provide a more tangible and meaningful forecast of what may happen.

The key features of the new reporting system and method in accordance with the present invention include, the application to complex treatment programs usually generating multiple significant events in each patient, the use of a uniform multimodality grading (severity ranking) system (CTCAE v3.0), the use of the median number of events (not incidence rates), the use of defined risk periods accounting for the longitudinal and recurring nature of some injuries, an emphasis on important high grade events, and the use of component and summary toxicity scores to compare global toxicity among treatment options within the same or similar cancer stage.

If one accepts the validity of the severity ranking system of the CTC, where all high-grade events are considered "severe" or "life-threatening", then for purposes of this classification system, any CTC grade 3-4 event could also be considered "important". However, we know that the use of grading systems in oncology has been inconsistent. Important adverse effects have not been captured in some trials and uniform reporting methods have been non-existent. Therefore, an effort must be made to ensure collection of "key toxicity elements" for each disease site, driven by the modalities involved. Reforming this step in the toxicity reporting process will require integration of TAME concepts in the design and conduct of clinical trails. This task may sound onerous but, once the multiple uses and benefits of toxicity staging have been articulated, this should be doable through buy-in from leadership at key federal institutions and cooperative groups.

The designation of "key toxicity elements" for each disease site is achieved through literature reviews and consensus panels to include clinicians, outcomes experts and patients/representatives of patient advocacy groups. A consensus workshop will be effective in establishing a limited list of key (important) events ("key TAME endpoints") for each disease site. These lists will then be used to develop screening tools and assessment methods. Developing guidelines for patient assessment, without making the process too onerous, will also require some work, but should be largely driven by the screening tools which focus on a limited number of key TAME endpoints for each disease site. Although key TAME endpoints will be the focus, all grade 3-4 effects of all types which occur during the trial will contribute to TAME outcome scores.

While many analogies to the TNM system apply, the TAME system and method in accordance with the present invention presents several significant improvements. The T, N, M domains are composed of rank order conceptual grades (e.g., T1-4) which are then arranged into tumor-specific groupings generated by outcome analysis. While T and N staging is becoming more precise with improvements in technology, we cannot quantitatively measure the exact amount of cancer. The whole integer value categories do not represent direct measurements of the impact on the host, only relative degrees of risk.

The TAME classification system provides access to much more direct information regarding the impact of toxicity on the host. The use of numerical values for the T, A and M domains are derived directly from clinical data, resulting in more meaningful information and utilities than that seen with the TNM system. Indeed, the individual components of T, A and M each communicate information about a different kind of risk, with the combined TAME score reflecting aggregate risk.

The TAME system is validated in retrospective data sets by correlations with a number of clinical outcomes as shown with reference to the table of FIG. 2. Six outcomes measures have been identified for investigation: the ability to complete treatment, QOL (quality of life), performance status, patient perception and physician perception of the degree of toxicity, and symptom index. Except for perhaps completion of therapy, these outcomes are not as unambiguous as survival. It is unlikely that a single outcome will be identified that will be accepted as the "ground truth" as solid as survival is for TNM. It is therefore proposed that only general correlations between TAME scores and individual outcome metrics need be demonstrated, and that the relationships between outcome measures and TAME scores may be viewed collectively for "validation" of the TAME system.

Each candidate outcome metric can be divided into 4 rank order groupings (classes or stages I-IV) and explored for relationships to TAME scores calculated for a number of treatment regimens. It is hypothesized that higher TAME scores will be seen in the higher outcome stages. It should also be possible to rank order TAME scores within a stage via kappa values. This may result in assigning a particular regimen or group of regimens to a risk "bin" analogous to the TNM system (T1N0, T1N1, etc). As with TNM staging, the patterns may not always line up perfectly, but such a distribution should demonstrate general relationships between clinical outcomes and TAME scores among the regimens.

The relationship between individual T, A and M values and individual outcome metrics can also be explored.

Completion of therapy is expected to be one of the strongest methods for validating the TAME system, but it may only show correlation with acute toxicity (T) and mortality (M), unless late consequential effects are operative. While QOL (quality of life) tools have been used to reflect the toxicity of a treatment program, they also reflect tumor activity. In addition, they encompass the diverse domains of social support and spirituality. QOL correlations with TAME scores therefore may be inconsistent, but will be explored. Performance status should generally correlate with global toxicity, especially during the acute phases of treatment (T). New clinical tools will need to be created for exploring patient and physician perceptions of global toxicity. Expert panels of physicians will be asked to rate (on a 4 point scale) and rank a group of treatment regimens known to them within their own field of expertise. Patients who have completed one of the same programs will also rate the "difficulty" of the treatment. We expect general correlations between patients and physicians, and between their respective ratings and TAME scores, but there will also be some outliers based on expected variations among individuals. Prospectively, one can explore correlation of TAME scores with standard tools that measure key symptom indexes (pain, fatigue, appetite, depression/anxiety).

Determining a "meaningful difference" between two or more treatment options with similar TAME scores will be an important task in development of the system. Class grouping of TAME scores via outcomes analysis will assist in determining cut-off points. As with TNM staging, cutoff points will need to be selected to group "like" regimens, otherwise you would have a continuous range of values. Simple numerical ranking within classes can also be done. The precise interpretation of TAME scores should become clear as real data is developed. In addition, two regimens may have the exact same TAME value but very different component values which require significant interpretation and judgment.

As the TAME system is validated (and tightly correlated) with other clinically relevant endpoints (completion of treatment, QOL, performance status, toxicity perceptions, symptom indexes) it may not be necessary to routinely collect so many types of outcomes measures in routine clinical trials.

It has been argued that the CTC has never been formally "validated". The TAME reporting system is founded on and consistent with the philosophy of the CTC grading system: to identify and separate serious from not so serious adverse effects, and to provide a method of examining a given treatment program for its toxicity "profile" (assorted types of toxicity) and frequency of adverse events. The CTC allows examination of both a single toxicity item as well as multiple toxicities. Although some toxicities are hard to directly measure and the reliability and validity of a given CTC scale may be challenged, many clinical effects can be well quantified and are considered well validated (e.g., lab values). In addition, as each version of the CTC has evolved, close attention has been paid to the consistency in severity ranking for each toxicity criteria. Therefore, while individual criteria may be challenged, in aggregate, the CTC should strongly reflect the degree of the intensity of global toxicity, and if consistently applied, should capture the majority of important changes experienced by the host. In this sense, validation of the TAME system will represent a validation of the CTC as system.

A number of utilities and associated benefits are projected for the TAME system as outlined in the table of FIG. 2 and further discussed in the following sections. These utilities and associated benefits including, but not limited to:

1) improved patient counseling and decision making in cancer treatment selection;

2) calculation of truly quantitative therapeutic ratios and other new metrics;

3) evaluation of palliative treatment options;

4) individual monitoring of toxicity during treatment;

5) a new safety reporting metric for sponsors, data monitoring committees, and IRBs;

6) pooling of toxicity data across multiple studies to improve the precision of risk estimates;

7) facilitating the development and selection of toxicity interventions;

8) and, it may provide an important new quality assurance metric

Physicians will likely find the most utility in comparison of TAME scores for determining treatment options, but patients may appreciate the information as well. The TAME system allows direct comparison of composite TAME scores as well as component scores among therapeutic options. In counseling a patient, citing the average number (and range) of serious events the "average" patient will experience while under treatment will be used to supplement the usual list of possible adverse effects, and their incidence. The use of the term "TAME" should have intuitive meaning to clinicians and laymen alike, suggesting that we can rate a particular treatment as "pretty tame" or "not so tame".

This should be of practical clinical utility in discussing therapeutic gain. For example, Dr. Smith proposes a given regimen which effects on a 5% increase in cure from (50-55%) but the TAME score suggests it is highly toxic. An alternative less toxic choice may be considered. Moreover, information regarding change in QOL with different TAME scores may help communicate even more about the global impact of cancer and its treatment.

The TAME system is the first system to allow one to calculate an actual therapeutic ratio, to determine therapeutic gain. There is also potential for the development of other novel metrics.

Therapeutic ratio: TR=Survival/TAME score

EXAMPLE

Treatment A: survival of 50% with a TAME score of 10 . . . 50/10=5

Treatment B: survival of 40% with a TAME score of 7 . . . 40/7=5.7

From simplistic view, Treatment B may be preferred if one looks only at the calculated treatment ratio based on the novel TAME score.

A number of mathematical models using various assumptions, weightings, standard gamble other approaches are additionally within the scope of the present invention.

Perhaps one of the most important uses of the TAME system will be in evaluating various palliative treatment options. This is certainly an area where toxicity is an overriding concern.

Pre-designated (benchmark) time points for calculating and comparing an individual who experiences a lot of toxicity (to published TAME scores) may be useful in early identification of outliers and sensitive individuals. It may offer an additional "gestalt" of how well or poorly a particular patient is tolerating therapy.

DSMBs, IRBs, and TMCs currently have a difficult time digesting a large amount of safety related data and making judgments about the "acceptability" of various toxicity profiles. Individual "T" and "M" scores may be calculated at "benchmark points" during treatment to monitor aggregate acute toxicity (e.g., TM-1mo, TM-2mo, etc) as a metric for safety monitoring in phase I and II trials. Full TAME scores at 1-2 years and beyond may be calculated for phase III trials. TM and TAME scores will reflect an overview and "gestalt" regarding the accumulating (and cumulative) toxicity of a given treatment program.

As noted in an FDA guidance on safety reporting, "For the most part, phase 2-3 trials are not designed to test hypotheses about safety . . . one can assume the available studies are under-powered . . . the approach is viewed more as exploration and estimation . . . pooling safety data across multiple trials can allow one to improve the precision of incidence estimates, i.e., narrow the confidence intervals."

This technique should also be applicable to TAME scores. Often, a same or similar treatment program is used in multiple studies, including pilot studies. Combining data on TAME scores may improve the accuracy of classification. In addition, pooling TAME data may allow one to generate hypotheses about risk among several putative factors including: gender, concomitant illness, drug factors (dose intensity), genetic profiles, socioeconomic status, geographic or institution setting. This may also be useful in identifying genetic predisposition to injury from one or more modalities.

Providing the range of TAME scores for all individuals in a treatment group would indicate the amount of variability. Publishing ranges in addition to the median number would also provide information on the low and high injury "experiences". Ranges in TAME scores may be calculated for an individual patient at any point in time. Pre-designated (benchmark) time points for comparing an individual who experiences a lot of toxicity (via comparison to published TAME scores) may be useful in early identification of outliers and sensitive individuals. Shift tables, scatter plots, box plots, cumulative distribution functions may all provide useful analytic tools.

Just as with decision-making regarding cancer therapeutics, information from TAME scores may guide choice of a toxicity intervention.

TAME global and component scores may be used to evaluate the impact of a specific toxicity intervention. A highly effective intervention against an "important" toxicity should generate a significant change in an individual component or TAME composite score, thus confirming its effectiveness. Once again, depending on the targeted toxicity and the context of the regiment, interpretation will be key. Reducing the risk of only one type of toxicity among many may produce little change in a component or global score, but hypothesis driven trials may use TAME scores as one of several key metrics of intervention activity. In addition, evaluating how individual toxicities contribute to the individual components or composite TAME scores may assist in identifying those toxicities with the greatest global impact on toxicity for intervention development. Alternatively, a given cancer treatment regimen may be intensified to achieve a similar TAME score with the expectation of higher cure rates.

Validation and incorporation of the TAME system into routine reporting could be a catalyst to pursue a broader set of scientific publication standards for toxicity reporting.

Although an increasingly amount of valuable data is now available in the literature, CONSORT standards and other advances in the complexity and scientific reporting have caused the length of journal publications to grow annually. Even with the advent of electronic publishing, there is limited space for displaying toxicity data. Routine inclusion of TAME scores will provide a shorthand way to communicate a great deal of information about the adverse event profile of a given regimen, and will supplement existing methods of toxicity reporting.

TAME endpoints and reports can be automatically collected and generated by customized software. Such software tools will also be important in automating and streamlining the data collection process.

The TAME system may have utility in other areas where multiple drugs are given or where treatments are more toxic (e.g., AIDS therapy, infectious diseases, and other life threatening illnesses)

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for determining a toxicity rating of a treatment program, the method comprising:
    identifying a toxicity grading system appropriate for the treatment program, wherein the toxicity grading system ranks the severity of adverse events related to a treatment program;
    recording significant adverse events occurring during an administration of the treatment program within a first predetermined period of time and recording significant adverse events occurring during the administration of the treatment program within a second predetermined period of time, wherein a significant adverse event is an adverse event ranked by the toxicity grading system as being severe or life-threatening and wherein the second predetermined period of time is after the first predetermined period of time;
    determining an acute toxicity domain of the treatment program by calculating a median number of significant adverse events occurring during the first predetermined period of time;
    determining an adverse late effects domain by calculating a median number of significant adverse events occurring during the second predetermined period of time;
    determining the toxicity rating of the treatment program from a sum of the acute toxicity domain and the adverse late effects domain; and
    comparing the toxicity rating of the treatment program with a toxicity rating of other treatment programs to determine a favorable treatment option for a patient;
    wherein each of the above method steps are performed according to an automated process using software tools.

2. The method of claim 1, wherein the toxicity grading system is a cancer toxicity grading system.

3. The method of claim 1, further comprising:
    determining a risk of treatment related mortality domain of the treatment program; and
    calculating a toxicity rating of the treatment program as a ratio of the risk of treatment related mortality domain to the sum of the acute toxicity domain, and the adverse late effects domain.

4. The method of claim 1, wherein the treatment program is a treatment program selected from the treatment program consisting of radiation, chemotherapy and surgery, radiotherapy, chemoradiotherapy.

5. The method of claim 1, wherein the first predetermined time period is from day one of the treatment program up to three months in duration of the treatment program.

6. The method of claim 1, wherein the second predetermined time period is more than three months after the start of the treatment program.

7. The method of claim 1, wherein a significant adverse event having a long duration is counted once in the determination of the median number of significant adverse events.

8. The method of claim 1, wherein the significant adverse event is a recurring significant adverse event, and each recurring significant adverse event is counted in the determination of the median number of significant adverse events.

9. The method of claim 3, wherein the step of determining the risk of treatment related mortality domain further comprises, determining the probability that a patient will die as a result of the treatment program.

10. The method of claim 3, further comprising the step of assigning a mathematical weight to the acute toxicity domain, the adverse late effect domain and the risk of treatment related mortality.

* * * * *